(12) United States Patent
Nikliborc

(10) Patent No.: US 7,241,196 B1
(45) Date of Patent: Jul. 10, 2007

(54) HEATED STUFFED ANIMAL

(76) Inventor: Stan Nikliborc, deceased, late of Fullerton, CA (US); by Marion Nikliborc, legal representative, 1909 E. Evergreen Ave., Fullerton, CA (US) 92835

( * ) Notice: Subject to any disclaimer, the term of this patent is extended or adjusted under 35 U.S.C. 154(b) by 0 days.

(21) Appl. No.: 11/096,629

(22) Filed: Apr. 1, 2005

Related U.S. Application Data

(60) Provisional application No. 60/558,843, filed on Apr. 2, 2004.

(51) Int. Cl.
*A63H 3/02* (2006.01)

(52) U.S. Cl. ...................... 446/369; 446/295

(58) Field of Classification Search .............. 446/14, 446/72, 77, 73, 295, 369, 390, 484; 219/200, 219/201, 430, 378, 439, 462, 528, 529, 549
See application file for complete search history.

(56) References Cited

U.S. PATENT DOCUMENTS

| | | | | |
|---|---|---|---|---|
| 1,558,278 A | * | 10/1925 | Phillips | 383/96 |
| 4,204,110 A | * | 5/1980 | Smit et al. | 392/443 |
| 4,954,676 A | * | 9/1990 | Rankin | 219/200 |
| 4,979,923 A | * | 12/1990 | Tanaka | 446/72 |
| 5,002,511 A | * | 3/1991 | Maki | 446/14 |
| 6,019,659 A | * | 2/2000 | Walters | 446/72 |
| 6,325,695 B1 | * | 12/2001 | Weiner | 446/369 |
| 6,488,561 B2 | * | 12/2002 | Weiner | 446/369 |
| 6,752,103 B1 | * | 6/2004 | Howell | 119/71 |

* cited by examiner

*Primary Examiner*—Nini F. Legesse
(74) *Attorney, Agent, or Firm*—Kenneth L Tolar

(57) ABSTRACT

A heated stuffed animal includes a head portion, a torso portion and a plurality of limbs. Embedded within the animal is a heater assembly including an encircling heating element extending from a battery casing that is accessible via a slit on the rear surface of the torso portion. The operating temperature and duration of the heater assembly can be selectively programmed with a pair of adjustable dials positioned on the casing.

6 Claims, 2 Drawing Sheets

HEATED STUFFED ANIMAL

CROSS REFERENCE TO RELATED APPLICATIONS

This application is entitled to the benefit of provisional application No. 60/558,843 filed on Apr. 2, 2004.

BACKGROUND OF THE INVENTION

The present invention relates to a heated stuffed animal that consoles and comforts a child.

DESCRIPTION OF THE PRIOR ART

Teddy bears and similar stuffed animals have been used to comfort and console children for many years. However, nothing consoles a child more than warmth, particularly when a parent is trying to lull a child to sleep. The present invention combines the advantages of both by providing a stuffed animal having a programmable heater therein for comforting and consoling a child.

SUMMARY OF THE INVENTION

The present invention relates to a heated stuffed animal. The device comprises a conventional stuffed animal design including a head, limbs and a torso portion. Embedded within the torso portion is a heater assembly having an encircling heating element attached thereto. The heater assembly includes a battery casing that is accessible via a slit formed on a rear surface of the torso portion. The heater assembly also includes a micro-controller, a digital thermal sensor and a heater driver. A timer selection dial and a temperature selection dial are positioned on the battery casing allowing a user to selectively program the heater's operating temperature and duration.

Accordingly, to use the above described device, a user preselects the operating duration and temperature using the respective selection dials. A power switch is activated whereby the stuffed animal will generate heat at the desired temperature and for the preselected duration.

It is therefore an object of the present invention to provide a heated stuffed animal that comforts and consoles a child.

It is another object of the present invention to provide a heated stuffed animal in which the operating duration and temperature can be preselected.

Other objects, features, and advantages of the present invention will become readily apparent from the following detailed description of the preferred embodiment when considered with the attached drawings and the appended claims.

DESCRIPTION OF THE PREFERRED EMBODIMENT

Figure 1:
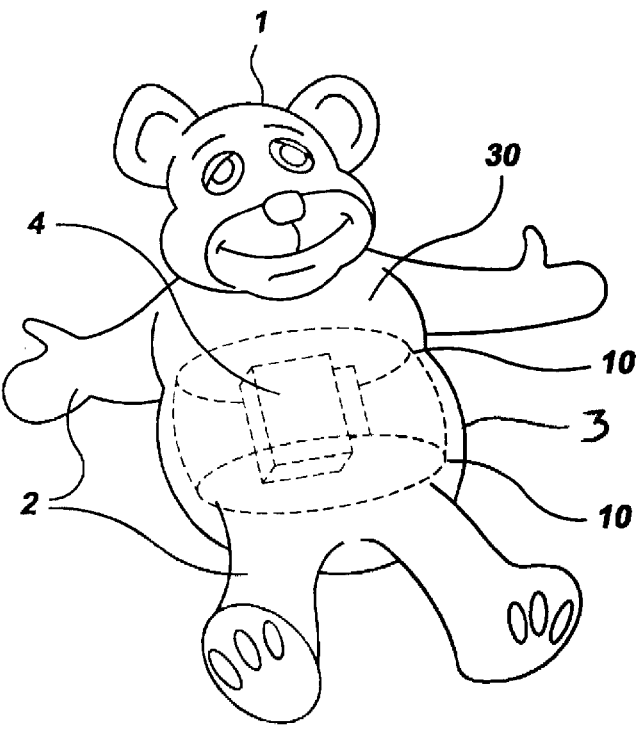
FIG. 1 is a front, perspective view of the heated stuffed animal according to the present invention.
Figure 2:
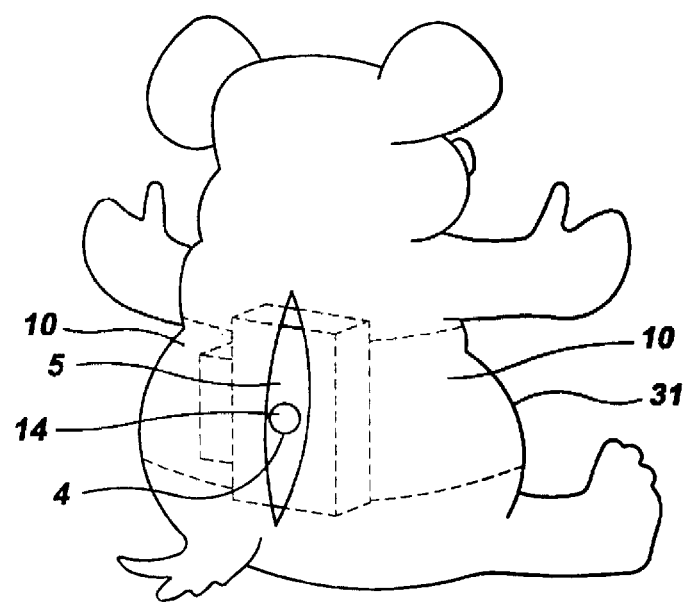
FIG. 2 is a rear, perspective view of the heated stuffed animal according to the present invention.
Figure 3:
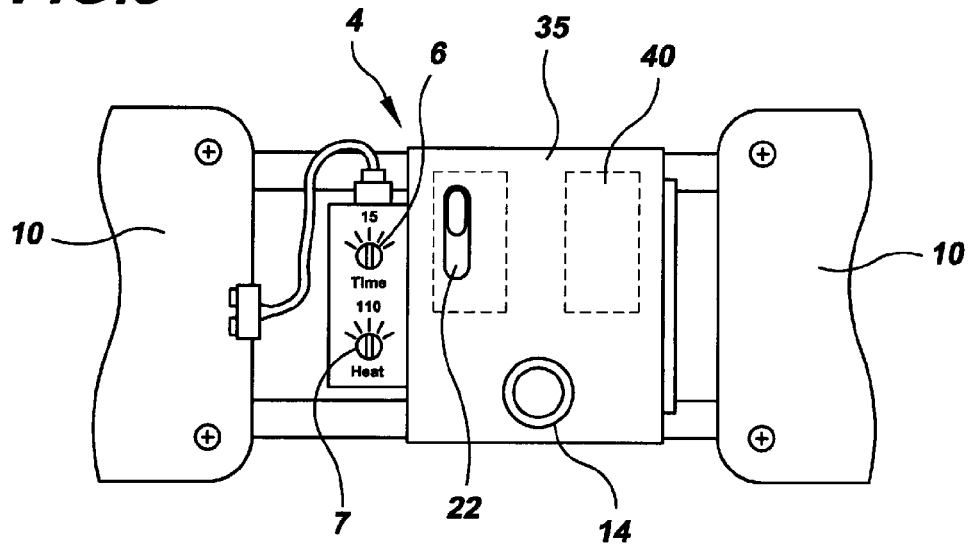
FIG. 3 is a detailed view of the heater assembly.

The present invention relates to a heated stuffed animal. The device comprises a conventional stuffed animal design including a head 1, limbs 2 and a torso portion 3. Embedded within the torso portion is a heater assembly for heating the animal to a desired temperature and for a desired duration. The heater assembly includes a battery casing 4 accessible via a slit 5 formed on a rear surface of the torso portion. The heater assembly also includes at least one flexible, neoprene heater band 10 attached to the casing that encircles the torso portion interior to concentrate heat at the front 30 and sides 31 thereof. Accordingly, the animal simulates a "warm heart" to console and comfort the child. Preferably, the neoprene heater is pliable but resilient so that it conforms to the animal's configuration if a child squeezes or contorts the animal. The heater is powered with batteries 40 removably housed within the casing. As such, a latch 22 releases an access panel 35 allowing a user to install or replace the batteries as necessary.

Figure 4:
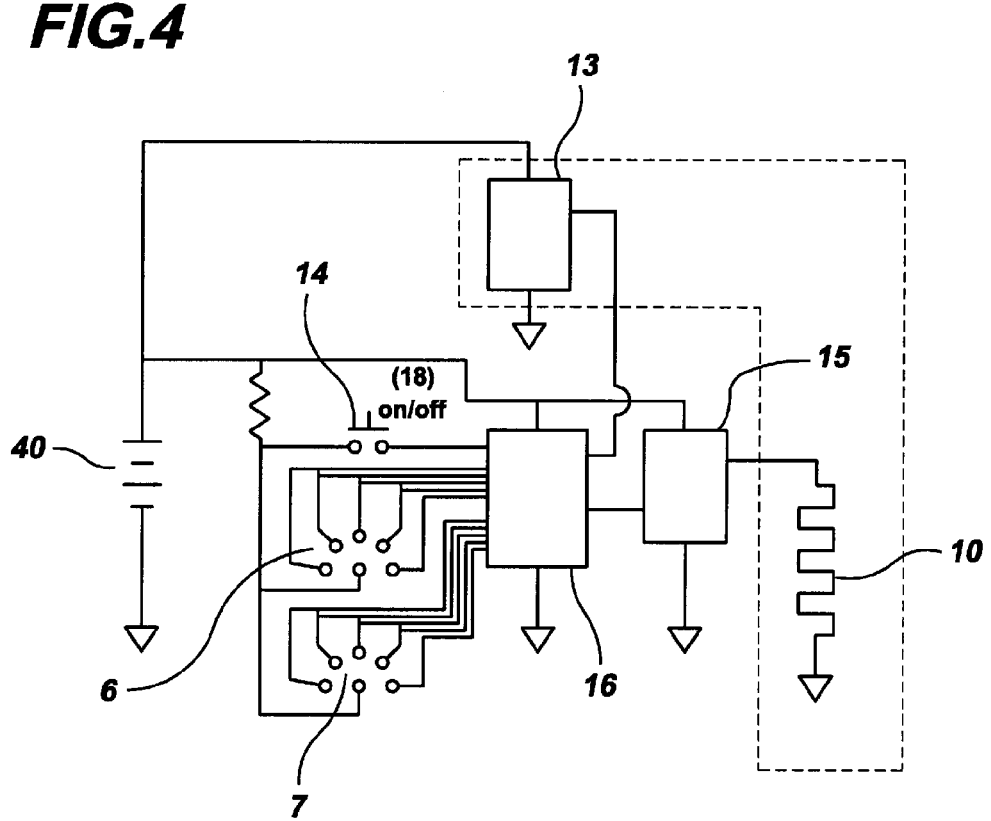
FIG. 4 is an electrical schematic of the heater assembly electronics.

A timer selection dial 6 and a temperature selection dial 7 are positioned on the battery casing that communicate with a micro-controller 16 allowing a user to preselect the operating temperature and duration of the heater. A digital thermal sensor 13 is positioned proximal the heater for providing localized temperature data to the micro-controller. As depicted in FIG. 4, a heater driver 15 establishes communication between the micro-controller and the heater.

Accordingly, to operate the above described device, a user preselects the operating duration and temperature of the heater using the respective selection dials. An activation button 14 is then depressed whereby the stuffed animal will generate heat at the selected temperature and for the preselected duration.

The above described device is not limited to the exact details of construction and enumeration of parts provided herein. For example, multiple heaters having any style or configuration can be used. Additionally, the construction and operation of the device can be simplified by eliminating the timer and temperature controls. In such event, the heater is activated by depressing the button 14; the heater will remain active until the button is depressed again. Finally, the size, shape and materials of construction of the various components can also be varied.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A heated stuffed animal comprising:
    a head, limbs and a torso portion;
    a heater means embedded within the torso portion for warming, comforting and consoling a person embracing the animal;
    means for automatically disabling said heater means after a selectively variable duration;
    means for automatically controlling an operating temperature range of said heater means.

2. The heated stuffed animal according to claim 1 wherein said means for automatically disabling said heater means after a selectively variable duration includes a microcontroller electrically connected to said heater means, a timer selection dial in communication with said microcontroller, said timer selection dial adjustable to instruct said microcontroller to disable said heater means after the selectively variable duration.

3. The heated stuffed animal according to claim 2 wherein said means for automatically controlling an operating temperature range of said heater means comprises:
   a digital temperature sensor positioned proximal said heater means for providing localized temperature data to the microcontroller;
   a temperature selection dial for preselecting a desired operating temperature range, said temperature selection dial in communication with said microcontroller, said temperature selection dial adjustable to instruct said microcontroller to enable and disable said heater means to maintain a localized temperature within the desired operating temperature range.

4. The heated stuffed animal according to claim 3 wherein said heater means further comprises a power source casing accessible via a slit formed on a rear surface of the torso portion, said casing having said temperature selection dial and said timer selection dial positioned thereon.

5. The heated stuffed animal according to claim 4 wherein said heating element encircles an interior portion of said torso portion.

6. The heated stuffed animal according to claim 5 wherein said heater element is a flexible neoprene heater band attached to said casing that encircles an interior surface of the torso portion to concentrate heat at two sides and a front of said torso portion to simulate a warm heart.

* * * * *